(12) United States Patent
Hong et al.

(10) Patent No.: US 8,663,315 B2
(45) Date of Patent: Mar. 4, 2014

(54) STENT FOR PROTECTING BIFURCATED BLOOD VESSELS IN BIFURCATION LESION

(75) Inventors: Myeong-Ki Hong, Seoul (KR); Yangsoo Jang, Seoul (KR); Dong Hoon Choi, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 13/508,916

(22) PCT Filed: Nov. 10, 2010

(86) PCT No.: PCT/KR2010/007905
§ 371 (c)(1),
(2), (4) Date: Jul. 23, 2012

(87) PCT Pub. No.: WO2011/059222
PCT Pub. Date: May 19, 2011

(65) Prior Publication Data
US 2012/0283821 A1 Nov. 8, 2012

(30) Foreign Application Priority Data
Nov. 12, 2009 (KR) .................. 10-2009-0109149

(51) Int. Cl.
*A61F 2/82* (2013.01)
(52) U.S. Cl.
USPC .................................... 623/1.34
(58) Field of Classification Search
USPC ............................... 623/1.15–1.38
See application file for complete search history.

(56) References Cited

U.S. PATENT DOCUMENTS

| | | | |
|---|---|---|---|
| 5,707,387 A * | 1/1998 | Wijay | 623/1.2 |
| 5,741,293 A * | 4/1998 | Wijay | 623/1.15 |
| 5,851,210 A | 12/1998 | Torossian | |
| 6,027,510 A | 2/2000 | Alt | |
| 7,686,846 B2 * | 3/2010 | Laborde et al. | 623/1.35 |
| 2002/0123794 A1 | 9/2002 | Ellis et al. | |
| 2004/0044399 A1 | 3/2004 | Ventura | |
| 2006/0074485 A1 | 4/2006 | Realyvasquez | |
| 2006/0217795 A1 * | 9/2006 | Besselink et al. | 623/1.15 |
| 2008/0161903 A1 * | 7/2008 | Sequin et al. | 623/1.11 |
| 2009/0182270 A1 | 7/2009 | Nanavati | |
| 2010/0241216 A1 * | 9/2010 | Rolando et al. | 623/1.16 |
| 2011/0060400 A1 * | 3/2011 | Oepen et al. | 623/1.15 |
| 2012/0029618 A1 * | 2/2012 | Tischler et al. | 623/1.16 |
| 2012/0116500 A1 * | 5/2012 | Jang et al. | 623/1.35 |

OTHER PUBLICATIONS

English Translation of the International Search Report mailed Jul. 29, 2011 for International Patent Application No. PCT/KR2010/007905.

* cited by examiner

*Primary Examiner* — Suzette J Gherbi
(74) *Attorney, Agent, or Firm* — Swanson & Bratschun, LLC

(57) ABSTRACT

The present invention relates to a stent for protecting a branch blood vessel at a branch-point lesion. The stent is inserted into and widened in a main blood vessel having the branch blood vessel extending in a slant from the branch-point lesion, thereby simultaneously expanding the main blood vessel and providing a smooth flow of blood towards the branch blood vessel. As a result, it is possible to simultaneously expand the main blood vessel and to sufficiently secure a passage from the main blood vessel towards the branch blood vessel. As such, the flow of blood is kept smooth. Further, after the stent is inserted into the main blood vessel, another stent, a guide wire, and related tools and catheter can be inserted in the direction of the branch blood vessel in a more accurate manner.

4 Claims, 4 Drawing Sheets

STENT FOR PROTECTING BIFURCATED BLOOD VESSELS IN BIFURCATION LESION

CROSS-REFERENCE TO RELATED APPLICATION

This application is a 35 U.S.C. §371 national phase application of PCT/KR2010/007905 (WO 2011/059222), filed on Nov. 10, 2010, entitled "Stent for Protecting Bifurcated Blood Vessels in Bifurcation Lesion", which application claims priority to and the benefit of Korean Patent Application No. 2009-0109149, filed Nov. 12, 2009, the disclosure of which is incorporated herein by reference in its entirety.

BACKGROUND

1. Field of the Invention

The present invention relates to a stent for blood vessels, and more particularly, to a stent for protecting a branch blood vessel at a branch-point lesion, in which radiopaque markers are formed between cells of the stent inside a main blood vessel so as to more safely protect the branch blood vessel and to insert an instrument such as a guide wire in the direction of the branch blood vessel in a more accurate and easy manner simultaneously, thereby allowing the stent to be guided to the location of an opening of the branch blood vessel.

2. Discussion of Related Art

In general, among a variety of diseases that attack the human body, when a disease narrows lumens in the human body to reduce their original function, or narrows blood vessels to restrict blood circulation, a medical instrument called a stent is inserted into and expands lumens or blood vessels.

Fat components are deposited on vessel walls of coronary arteries, and the resultant inflammation reaction gradually narrows lumens of the coronary arteries. The narrowed lumens of the coronary arteries obstruct sufficient supply of blood to the heart muscle (myocardium), which causes coronary artery disease or ischemic heart disease.

When blood is not sufficiently supplied to the myocardium, cardialgia, dyspnea, and other symptoms occur according to the extent of the deficiency in the supply. This coronary artery disease develops into a clinical manifestation such as angina pectoris, acute myocardial infarction, or sudden cardiac death.

Percutaneous coronary intervention (PCI) is a therapeutic method that physically expands the lumens of coronary arteries which are narrowed by the deposits of cholesterol on walls of blood vessels using a balloon catheter or a stent. However, the percutaneous transluminal coronary angioplasty using the balloon catheter may cause typical complication such as acute coronary occlusion or artery dissection.

In contrast, the therapeutic method using the stent can prevent the acute coronary occlusion and the artery dissection that may be caused by the therapeutic method using the balloon catheter. In the case of coronary artery branch-point lesions, this stent intervention fails to contribute to reduction in restenosis of blood vessels.

FIG. 1 is a conceptual diagram showing a coronary artery branch-point lesion B in which stenosis occurs at proximal and distal sections 1a and 1b of a main blood vessel 1 and a boundary of a branch blood vessel 2. The branch blood vessel 2 is inclined on one side of the main blood vessel 1 in spatial connection with the main blood vessel 1. An open boundary between the main blood vessel 1 and the branch blood vessel 2 is referred to as an opening H of the branch blood vessel 2.

When severe stenosis is found to occur at the main blood vessel 1 in the coronary artery branch-point lesion, a stent 3 is inserted into the main blood vessel 1. The stent 3 is contracted when inserted, and then is expanded by a balloon catheter 6. Thereby, the stent 3 remarkably reduces the severe stenosis of the main blood vessel 1 and is supported on an inner wall of the main blood vessel 1. The stent 3 is made up of a plurality of cells 4. The cells 4 may generally include a single open cell and a plurality of closed cells, either of which has a rhombic cross section and a root and a crest.

The stent 3 inserted in this way is disposed across the opening H of the branch blood vessel 2, as shown in FIG. 1.

Here, the stent 3 runs across the opening H of the branch blood vessel 2. Thus, depending on how many cell wires of the stent 3 are located at the opening, it determines whether the flow of blood between the main blood vessel 1 and the branch blood vessel 2 is obstructed. If the cell wires of the stent are densely located at the opening H of the branch blood vessel, this presents an obstacle to the flow of blood to the branch blood vessel. This results in a poor clinical outcome.

Thus, when this situation occurs, it is necessary to insert the balloon catheter into the stent 3 that has been inserted into the main blood vessel 1, to expand the inserted balloon catheter to widen the cells 4 of the stent 3. That is, since an interval between the cells 4 of the stent 3, which is located at the opening H, are expanded to secure a wider passage towards the branch blood vessel 2. Thereby, the flow of blood towards the branch blood vessel is made smoother.

In FIG. 2, it is shown that the stent 3 is inserted into the main blood vessel 2. Here, C1 indicates a single open cell, and C2 indicates a plurality of closed cells. As can be seen from FIG. 2, the single open cell C1 is larger than each of the plurality of closed cells C2.

In this case, the balloon catheter 6 inserted into the stent 3 should be positioned and expanded in the open cell C1 or between the closed cells C2 so as to widen the interval between the cells. Preferably, an area between the cells expanded in this way should be larger than that of the opening H. Thereby, the flow of blood towards the branch blood vessel can be kept smooth. Further, another stent, a guide wire, related tools, and a catheter can be inserted into the branch blood vessel 2 via the main blood vessel 1 in an accurate and easy manner.

However, this related art has the following problems.

When the stent 3 is inserted into the main blood vessel 1, the major cause of obstruction of the smooth flow of blood towards the branch blood vessel 2 is derived from the many cell wires that are distributed around the opening H of the branch blood vessel 2 in a undesired pattern against the smooth flow of blood. When the stent 3 is inserted into the main blood vessel 1 using a typical method, it is impossible to ascertain how the cell wires of the stent 3 are disposed at the opening H of the branch blood vessel 2.

First, just before the stent 3 is inserted into and expanded in the main blood vessel 1, efforts should be made to prevent the cell wires of the stent 3 from being disposed at the opening H of the branch blood vessel 2 or to dispose the cell wires of the stent 3 at the opening H of the branch blood vessel 2 as little as possible. Nevertheless, when the stent 3 is inserted by typical intervention, it is impossible to ascertain a positional relation between the cell wire and the opening of the branch blood vessel.

Second, to enable the blood to smoothly flow towards the branch blood vessel 2, the guide wire passes through the single open cell C1, if possible, after the stent 3 is inserted into the main blood vessel 1, and the balloon expansion occurs at the single open cell. Thereby, a wider passage by which the opening H of the branch blood vessel 2 is not restricted is secured to provide a desired flow of blood towards the branch blood vessel 2.

However, in the typical intervention using the conventional stent 3, when the guide wire is inserted towards the branch blood vessel 2 after the stent is inserted into the main blood vessel 1, it is impossible to ascertain through which one of the single open cell C1 and the plurality of closed cells C2 the guide wire passes. As one example, the balloon catheter 6 is generally inserted at a position corresponding to the opening H of the branch blood vessel 2, and then it is positioned and expanded between the cells. If the balloon catheter 6 is expanded when the closed cells C2 having a relatively small size are located at the opening H, there is a limit to widening the interval between the cells, as shown in FIGS. 3 and 4. Thus, even after the balloon catheter 6 is expanded, the flow of blood introduced into the branch blood vessel 2 may be obstructed because the area of each closed cell C2 is smaller than that of the opening H of the branch blood vessel 2. Further, when another surgical instrument such as another stent is inserted later, the instrument may get caught on one of the closed cells C2.

SUMMARY OF THE INVENTION

Accordingly, the present invention has been made to solve the above-mentioned problems occurring in the related art, and the present invention provides a stent for a smooth flow of blood introduced into a branch blood vessel when the stent is inserted into a main blood vessel at a blood vessel branch-point lesion.

The technical problems to be solved in the present invention are not limited to the aforementioned technical problems, and other non-mentioned technical problems will be clearly understood by those skilled in the art from the following description.

An aspect of the present invention provides a stent for protecting a branch blood vessel at a branch-point lesion, which is inserted into and widened in a main blood vessel having the branch blood vessel extending in a slant from the branch-point lesion, and thereby expanding the main blood vessel. At least two radiopaque markers are formed in a circumferential direction of the stent.

The markers may be disposed in threes at intervals of 120° in the circumferential direction of the stent.

The stent may include ties connecting a plurality of cell wires disposed in a lengthwise direction thereof.

Each of the markers may be formed at one side of the tie.

Another aspect of the present invention provides a stent for protecting a branch blood vessel at a branch-point lesion, which is inserted into and widened in a main blood vessel having the branch blood vessel extending in a slant from the branch-point lesion, and thereby expanding the main blood vessel. Radiopaque markers are respectively formed on cells that are adjacent to each other in a lengthwise direction of the stent.

The stent may further include at least two radiopaque markers formed in a circumferential direction thereof.

The markers formed in the circumferential direction may be disposed in threes at intervals of 120°.

The markers may be formed of at least one selected from the group consisting of stainless steel, gold, and platinum.

The stent may be formed of at least one selected from the group consisting of stainless steel, cobalt, titanium, platinum, and an alloy thereof.

Yet another aspect of the present invention provides a stent for protecting a branch blood vessel at a branch-point lesion, which is inserted into and widened in a main blood vessel having the branch blood vessel extending in a slant from the branch-point lesion, and thereby expanding the main blood vessel. The stent includes: a plurality of cell wires disposed in a lengthwise direction of the stent; ties connected between the cell wires; and at least two radiopaque markers, which are each formed at one side of each tie, and which are formed in a circumferential direction of the stent.

Each cell wire may have a zigzag shape in a widthwise direction.

The markers may be disposed in threes at intervals of 120° in the circumferential direction of the stent.

The stent may include cells, which are to be widened between the cell wires and the ties and which include first cells and second cells having a relatively smaller size than the first cells.

The markers may be formed on the respective ties between the first cells.

The stent may further include other radiopaque markers formed on the respective cells that are adjacent to each other in a lengthwise direction thereof.

The markers may be formed of at least one selected from the group consisting of stainless steel, gold, and platinum.

The stent may be formed of at least one selected from the group consisting of stainless steel, cobalt, titanium, platinum, and an alloy thereof.

In the present invention, three radiopaque markers are formed on the ties, which are connected between the cell wires, in a circumferential direction of the stent inserted into the main blood vessel; and other markers are formed on the respective cells, which are adjacent to each other, in a lengthwise direction of the stent. Thus, when a surgeon inserts the stent, the stent is positioned across the opening of the branch blood vessel. In this state, even when the stent is slightly adjusted, the stent can be guided so that a desired portion of the stent is properly positioned at the opening of the branch blood vessel. Then, a guide wire and a balloon catheter are inserted into a single open cell of the stent corresponding to a space between the markers, and an interval between the other cells can be effectively widened.

Consequently, it is possible to sufficiently secure a passage from the main blood vessel towards the branch blood vessel. As such, the flow of blood is kept smooth, and another stent, a guide wire, and related tools and catheter can be additionally inserted in the direction of the branch blood vessel in a more accurate and easy manner.

BRIEF DESCRIPTION OF THE DRAWINGS

The above and other objects, features and advantages of the present invention will become more apparent to those of ordinary skill in the art by describing in detail the exemplary embodiments thereof with reference to the attached drawings, in which.

DETAILED DESCRIPTION OF EXEMPLARY EMBODIMENTS

Hereinafter, an exemplary embodiment of a stent for protecting branch blood vessel at branch-point lesion in accordance with the present invention will be described with reference to the accompanying drawings.

Figure 1:
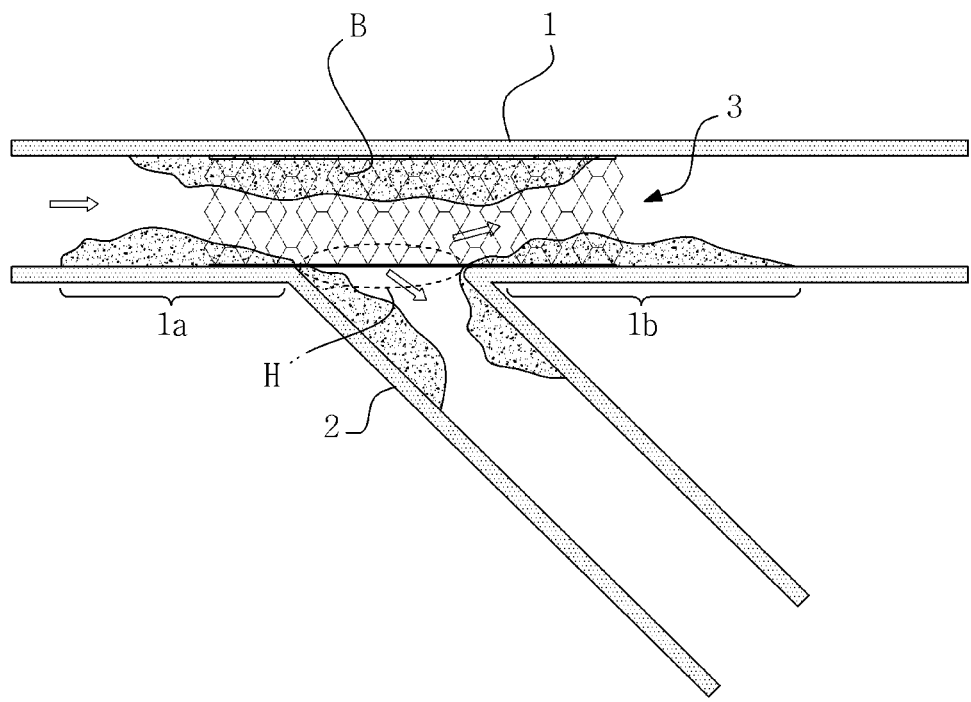
FIG. 1 is a conceptual diagram showing a coronary artery branch-point lesion B.
Figure 2:
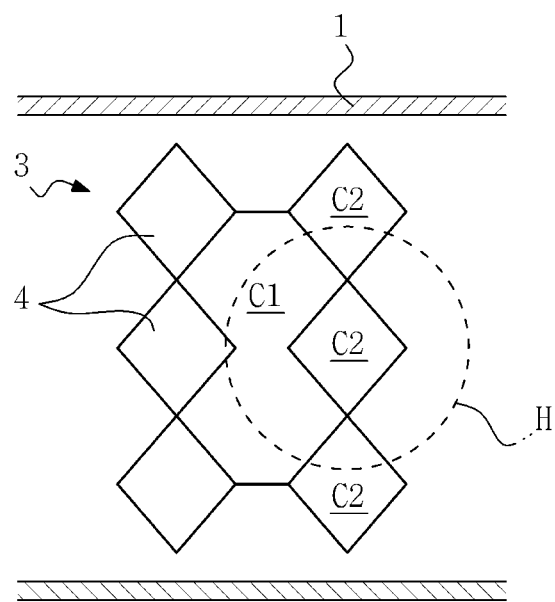
FIG. 2 is a conceptual diagram showing a state in which a stent is inserted into a main blood vessel according to the related art.
Figure 3:
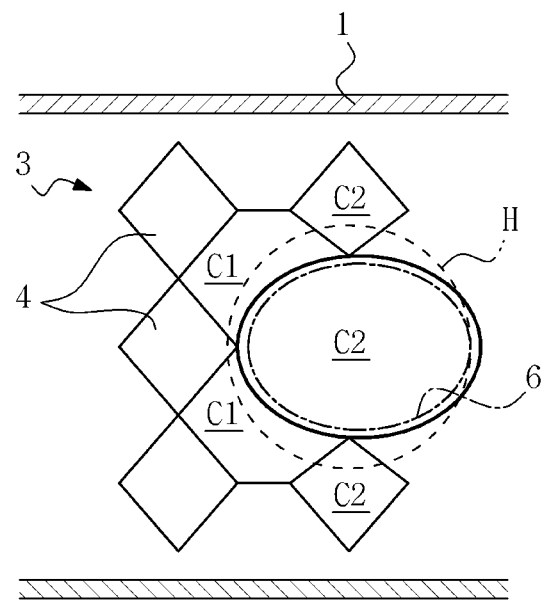
FIGS. 3 and 4 are conceptual diagrams showing how a cell is widened by a balloon catheter in the event of stent intervention in the related art.
Figure 4:
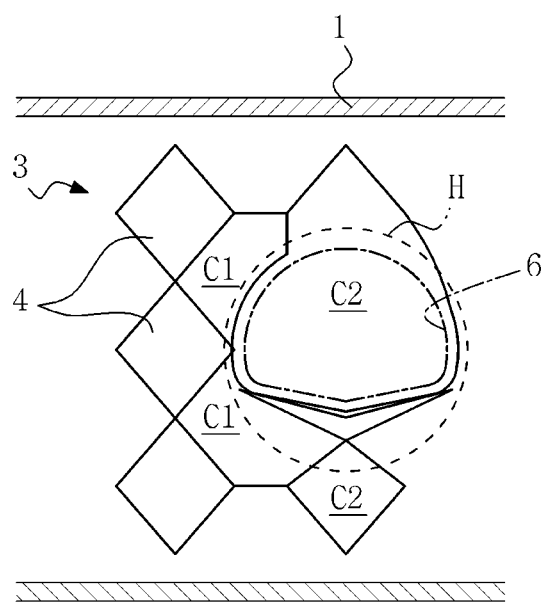
Figure 5:
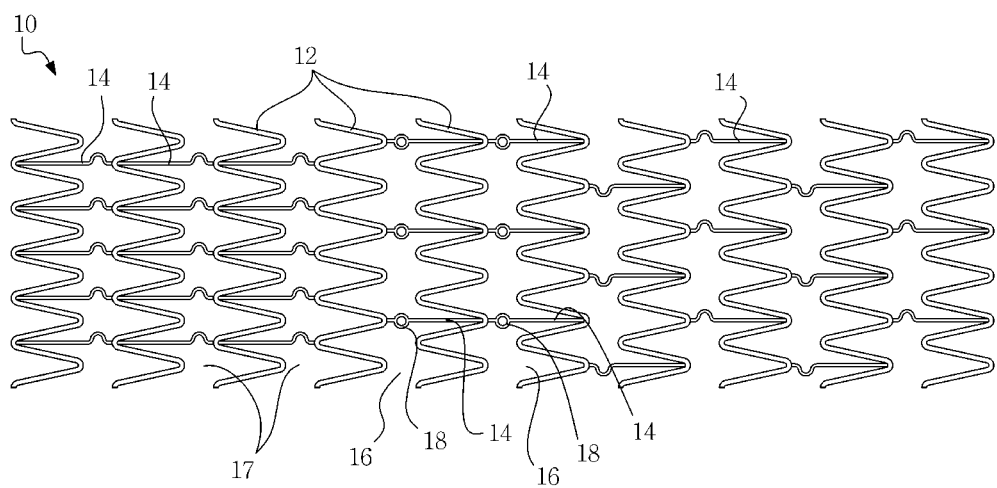
FIG. 5 is a development diagram showing an unfolded stent according to an embodiment of the present invention.
Figure 6:
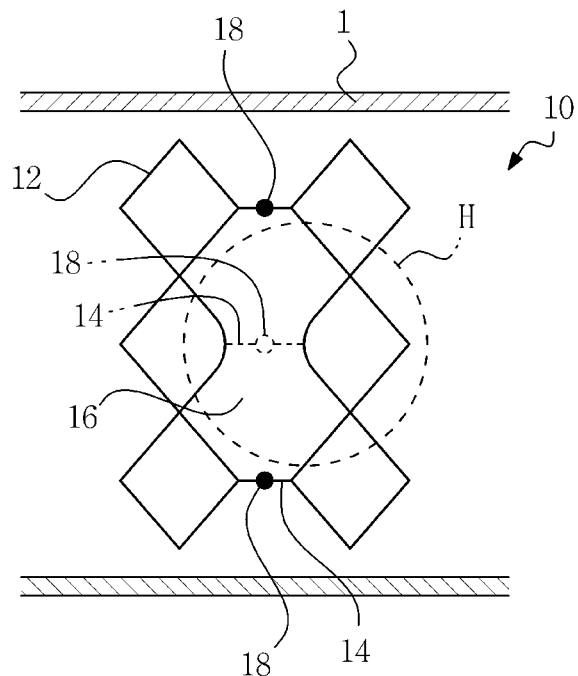
FIG. 6 is a development diagram showing an inserted stent according to an embodiment of the present invention.

FIG. 5 is a development diagram showing an unfolded stent according to an embodiment of the present invention, and FIG. 6 is a development diagram showing an inserted stent according to an embodiment of the present invention. Hereinafter, the same configurations as in the related art will be described with reference to FIGS. 1 to 4.

As shown in these figures, a stent 10 for a main blood vessel 1 according to an embodiment of the present invention includes a plurality of cell wires 12 disposed in a lengthwise direction thereof, ties 14 connected between the cell wires 12, and at least two radiopaque markers 18 provided in a circumferential direction of the stent.

In the event of intervention, the stent 10 is inserted into the main blood vessel 1 and comes into close contact with an inner wall of the main blood vessel 1. In this manner, the close contacted stent 10 serves to expand the blood vessel to improve blood circulation. The stent 10 may be formed of at least one selected from the group consisting of stainless steel, cobalt, titanium, platinum having predetermined rigidity and elasticity, and an alloy thereof.

The cell wires 12 are disposed at regular intervals in a lengthwise direction of the stent 10. The cell wires 12 form an overall framework of the stent 10, and have a zigzag shape in a widthwise direction. That is, each cell wire 12 has a shape in which a plurality of roots and crests are repeated.

Next, the ties 14 are connected between the cell wires 12. The ties 14 are formed in the lengthwise direction of the stent 10 by a predetermined length. The ties 14 are integrally formed with the cell wires 12 and are provided at regular intervals in a circumferential direction of the stent 10. When the stent 10 is expanded by a balloon catheter 20 to be described below, the ties 14 are expanded along with the cell wires 12, and come into close contact with the inner wall of the main blood vessel 1.

Cells 16 and 17 having partitioned spaces are defined between the cell wires 12 and the ties 14 described above. The size and cross section of each of the cells 16 and 17 may be generally decided according to the degree of expansion required in consideration of a diameter of the main blood vessel 1. Referring to FIG. 5, the size of the first cell 16 is larger than that of the second cell 17. This is because the ties 14 connecting the cell wires 12 have different lengths. That is, the first cells 16 having a relatively larger size are formed on regions where the ties 14 are long, whereas the second cells 17 having a relatively smaller size are formed on regions where the ties 14 are short.

In this manner, since the cells 16 and 17 have different sizes, the first cell 16 having a large size should be placed at the opening H of the branch blood vessel 2, and then be expanded, so that the passage to the branch blood vessel 2 can be sufficiently secured.

The ties 14 located at the first cells 16 are provided in threes at regular intervals in a circumferential direction. Since the three ties 14 are located in the circumferential direction of the cylindrical stent 10, each tie has an interval of 120°.

Each tie 14 configured in this way is provided with a radiopaque marker 18 at one side thereof. These markers 18 function to guide the location of the stent 10, and to accurately position the cell 16 on the opening H of the branch blood vessel 2. The markers 18 may be formed of metal or resin through which no radiation passes. For example, the markers 18 may be formed of at least one selected from the group consisting of stainless steel, gold, and platinum. Since the markers 18 are opaque to the radiation, it is easy for a surgeon to check the location of the stent 10 outside of a human body.

Figure 7:
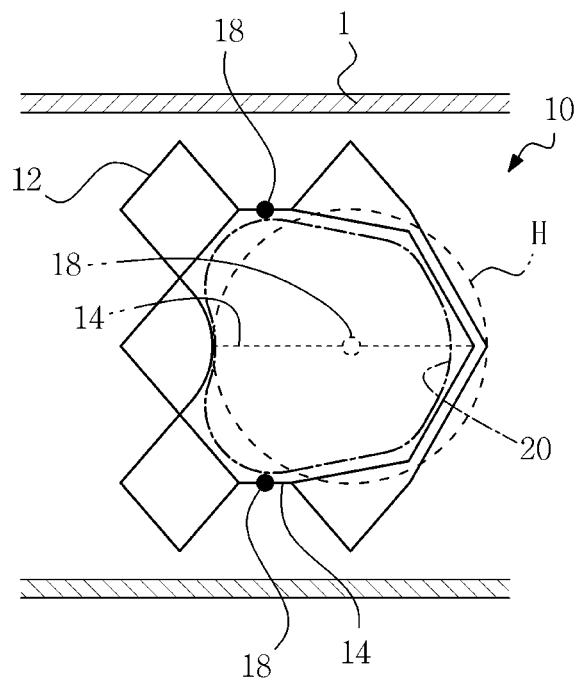
FIG. 7 is a conceptual diagram showing how a cell of the stent is widened by a balloon catheter according to an embodiment of the present invention.

In the present embodiment, the markers 18 located at the respective ties 14 are preferably provided in threes in a circumferential direction. This is intended to allow the first cell 16 to be positioned so as to correspond to the opening H when the stent 10 is inserted into the main blood vessel 1. In detail, when the first cell 16 is positioned so as to correspond to the opening H as in FIG. 6, the surgeon inserts a guide wire and a balloon catheter 20 to widen the first cell 16. Then, as in FIG. 7, the first cell 16 can be widened so as to have a size that is equal to or larger than that of the opening H. For reference, in FIG. 6, the marker 18 is indicated by a dotted line. This means that the marker 18 is located on the opposite side That is to say, since the first cell 16 and the opening H are accurately centered, the first cell 16 and the opening H are spatially connected when the balloon catheter 20 is expanded, thereby making the flow of blood smooth. However, when the balloon catheter 20 is expanded in the state of which the first cell 16 and the opening H are not centered, i.e., deviate from each other, this may cause a problem. That is, even when the first cell 16 is widened, part of the ties 14 is located on the opening H, so that the blood cannot smoothly flow due to obstruction of the first cell 16.

Thus, in the present embodiment, the markers 18 are formed at three portions in the circumferential direction. Thereby, even when the first cell 16 is not accurately centered, the first cell 16 can be easily centered with respect to the opening H by rotating the stent 10 at a predetermined angle only, as in FIG. 6. Thus, the passage from the main blood vessel 1 towards the branch blood vessel 2 can be sufficiently secured, so that the blood can smoothly flow without interference with the stent 10. Further, another stent, a guide wire, and related tools and catheter are easily inserted through the sufficiently secured passage.

Further, since each marker 18 is formed between the first cells 16 having a relatively large size, a passage whose size is sufficiently large can be secured when the first cells 16 are widened.

Meanwhile, the markers 18 are not necessarily provided to the ties 14 and may be formed at the cell wire 12 themselves.

To detect a relation between the front and the rear of the stent or between the proximal and distal parts of the stent, the markers 18 are preferably formed in pairs at the cells 16 and 17 that are adjacent to each other in the lengthwise direction of the stent 10. This is intended to easily guide the stent to the location of the opening H through the markers 18. That is, the surgeon looks at the markers 18 formed adjacent to each other outside the human body, guides the stent to the location of the opening H of the branch blood vessel 2, and expands the balloon catheter 20, thereby widening the first cell 16.

The stent 10 of the present invention is not limited to the aforementioned embodiment. The markers may be provided in fours in the circumferential direction of the stent 10. In this case, in comparison with the aforementioned embodiment, the interval of the first cell 16 defined between the ties 14 becomes smaller, and thus it is difficult to spatially connect the first cell with the opening H. This modification may be applied depending on the design conditions.

While the invention has been shown and described with reference to certain exemplary embodiments thereof, it will be understood by those skilled in the art that various changes in form and details may be made therein without departing from the scope of the invention as defined by the appended claims.

What is claimed is:

1. A stent for protecting a branch blood vessel at a branch-point lesion, which is inserted into and widened in a main blood vessel having the branch blood vessel extending in a slant from the branch-point lesion, and thereby expanding the main blood vessel, the stent comprising:
   a plurality of cell wires disposed in a lengthwise direction of the stent;
   ties connected between the cell wires; and
   at least two radiopaque markers, which are each formed at one side of each tie, and which are formed in a circumferential direction of the stent, wherein the stent includes cells, which are to be widened between the cell wires and the ties, and include first cells and second cells having a relatively smaller size than the first cells, wherein the second cells are formed in areas where the ties between the cell wires are shorter relative to the ties between the cell wires in the first cells,
   wherein the markers are formed on the respective ties between the first cells,
   wherein the markers are disposed in threes at intervals of 120° in the circumferential direction of the stent,
   wherein the stent further includes other radiopaque markers formed on the respective cells that are adjacent to each other in a lengthwise direction thereof.

2. The stent for protecting a branch blood vessel at a branch-point lesion according to claim 1, wherein each cell wire has a zigzag shape in a widthwise direction.

3. The stent for protecting a branch blood vessel at a branch-point lesion according to claim 1, wherein the markers are each formed of at least one selected from the group consisting of stainless steel, gold, and platinum.

4. The stent for protecting a branch blood vessel at a branch-point lesion according to claim 1, wherein the stent is formed of at least one selected from the group consisting of stainless steel, cobalt, titanium, platinum, and an alloy thereof.

* * * * *